US009907568B2

(12) United States Patent
Tramboo et al.

(10) Patent No.: US 9,907,568 B2
(45) Date of Patent: Mar. 6, 2018

(54) PERCUTANEOUS METHODS FOR SPINAL STENOSIS AND FORAMINAL STENOSIS

(71) Applicant: SPINELOOP LLC, Newport Beach, CA (US)

(72) Inventors: Tariq Ahmad Tramboo, Srinagar (IN); Ashraf Taha, Irvine, CA (US)

(73) Assignee: SPINELOOP, LLC, Newport Beach, CA (US)

( * ) Notice: Subject to any disclaimer, the term of this patent is extended or adjusted under 35 U.S.C. 154(b) by 0 days.

(21) Appl. No.: 15/432,609

(22) Filed: Feb. 14, 2017

(65) Prior Publication Data

US 2017/0150989 A1    Jun. 1, 2017

Related U.S. Application Data

(62) Division of application No. 13/551,166, filed on Jul. 17, 2012.

(60) Provisional application No. 61/508,999, filed on Jul. 18, 2011.

(51) Int. Cl.
| | | |
|---|---|---|
| *A61B 17/34* | (2006.01) | |
| *A61B 17/14* | (2006.01) | |
| *A61M 5/142* | (2006.01) | |
| *A61N 1/05* | (2006.01) | |

(Continued)

(52) U.S. Cl.
CPC ........ *A61B 17/3401* (2013.01); *A61B 17/149* (2016.11); *A61M 5/14276* (2013.01); *A61N 1/0551* (2013.01); *A61B 17/1671* (2013.01); *A61B 2017/00039* (2013.01); *A61B 2017/00084* (2013.01); *A61B 2017/00557* (2013.01); *A61B 2217/005* (2013.01)

(58) Field of Classification Search
CPC .............. A61B 17/149; A61B 17/1659; A61B 17/1671; A61B 2017/320004; A61B 2017/32006
See application file for complete search history.

(56) References Cited

U.S. PATENT DOCUMENTS

| | | | |
|---|---|---|---|
| 4,643,178 | A | 2/1987 | Nastari et al. |
| 7,553,307 | B2 | 6/2009 | Bleich et al. |
| 2006/0089609 | A1 | 4/2006 | Bleich |

(Continued)

FOREIGN PATENT DOCUMENTS

| | | |
|---|---|---|
| WO | 2006044727 A2 | 4/2006 |
| WO | 2008070867 A2 | 6/2008 |

*Primary Examiner* — Samuel Hanna
(74) *Attorney, Agent, or Firm* — Troutman Sanders LLP

(57) ABSTRACT

The present invention is a method for performing a percutaneous laminoplasty that includes entering a first introducer needle introducing a first tool wire into an epidural space above a selected lamina, entering a first catcher exit needle that that is caught with the first introducer needle and pulled through a patient body and entering a second introducer needle introducing a second tool wire into the epidural space below the selected lamina. The method also includes entering a second catcher exit needle that is caught within the epidural space and pulled through the patient body, moving the caught first introducer needle and the first catcher exit needle back and forth to cut the lamina and moving the caught second introducer needle and the second catcher exit needle back and forth to cut the lamina. There is also a method for performing a percutaneous foraminoplasty.

18 Claims, 16 Drawing Sheets

(51) Int. Cl.
   *A61B 17/16*   (2006.01)
   *A61B 17/00*   (2006.01)

(56) References Cited

U.S. PATENT DOCUMENTS

| | | |
|---|---|---|
| 2006/0089633 A1* | 4/2006 | Bleich ................ A61B 17/1659 606/32 |
| 2008/0275458 A1 | 11/2008 | Bleich |
| 2009/0177241 A1* | 7/2009 | Bleich ................ A61B 17/1671 606/86 R |
| 2010/0324575 A1 | 12/2010 | Chan |
| 2011/0060314 A1 | 3/2011 | Wallace |
| 2011/0257671 A1 | 10/2011 | Trovato et al. |
| 2013/0023880 A1 | 1/2013 | Tramboo et al. |

* cited by examiner

1400

Entering a first introducer epidural needle that
includes a proximal end outside of the patient, a distal end,
a first hollow internal diameter and a first penetrating perforating tip,
the first penetrating perforating tip is disposed on the distal end,
the first hollow internal diameter allows one or more first wire tools
to pass through the introducer epidural needle, the first penetrating
perforating tip is percutaneously placed into an epidural space
of a spine on a first side allowing the one or more first
wire tools to be introduced and entered
into the epidural space of a selected right lamina of the
spine above a targeted vertebra
with a side, where a spinous process divides a right lamina
and a left lamina of the target lamina
1410

▼

Entering a first exit epidural needle that includes a proximal end
outside of the patient, a distal end, a second hollow internal diameter
and a second penetrating perforating tip, the second penetrating perforating
tip is disposed on the distal end, the second hollow internal diameter
allows a one or more second wire tools to pass through the exit epidural
needle, the second penetrating perforating tip is percutaneously placed into
the epidural space of the spine
that introduces and enters the second wire tools below the selected right lamina
of the side of the targeted vertebra where the first introducer epidural needle is
entered in the epidural space of
the spine above the selected right lamina, the first penetrating perforating tip and
the second penetrating perforating tip in the epidural space
resulting in the first penetrating perforating
tip and the second penetrating perforating tip facing each other, the
first penetrating perforating tip and the second penetrating perforating
tip centering the right lamina
1420

 

Introducing a first hook-like grasper tool with a distal end and a proximal end outside of the patient, the distal end of the first hook-like grasper tool is a selected one of manually extended and mechanically extended through the first hollow internal diameter of the first exit epidural needle, the distal end of the first hook-like grasper tool attaches the one or more first wire tools introduced through the first introducer epidural needle within the epidural space, the one or more first wire tools and the first hook-like grasper tool are pulled through the first exit epidural needle and out of a patient body, the attached the first hook-like grasper tool and the one or more first wire tools engaging below the selected right lamina of the target vertebra, where a spinous process divides the right lamina and the left lamina, the one or more first wire tools having a curved middle portion, the curved middle portion lying adjacent to the inferior aspect of the right lamina, the curved middle portion cuts the right lamina of the target vertebra in an anterior to posterior direction
1430

Entering a second introducer epidural needle that includes a proximal end outside of the patient, a distal end, a third hollow internal diameter and a third penetrating perforating tip disposed on the distal end, the third hollow internal diameter allows one or more third wire tools to pass through the second introducer epidural needle, the third penetrating perforating tip is percutaneously placed into the epidural space of the spine allowing the one or more third wire tools to be introduced and entered into the epidural space of a selected left lamina of the spine above a targeted vertebra with a side, where a spinous process divides the right lamina and the left lamina
1440

Entering a second exit epidural needle that includes a proximal end outside of the patient, a distal end, a fourth hollow internal diameter, a fourth penetrating perforating tip disposed on the distal end that is a selected one of manually extended and mechanically extended, the fourth hollow internal diameter allows a selected one or more fourth wire tools to pass through the second exit epidural needle, the fourth penetrating perforating tip is percutaneously placed into the epidural space of the spine that introduces and enters the one or more fourth wire
tools below the side of the targeted vertebra where the second introducer epidural needle is entered in the selected epidural space of the spine of the selected left lamina, the third
penetrating perforating tip and the fourth penetrating perforating tip in the epidural space resulting
in the third penetrating perforating tip and the fourth penetrating perforating tip facing each other, the third penetrating perforating tip and the fourth penetrating perforating tip centering the left lamina
1450

▼

Introducing a second hook-like grasper tool with a distal end and a proximal end outside of the patient, the distal end of the second hook-like grasper tool is a selected one of manually extended and mechanically extended through the fourth hollow internal diameter of the second exit epidural needle, the second hook-like grasper tool attaches the selected one or more third wire tools introduced through the second introducer epidural needle within the epidural space, the selected one or more third wire tools is
pulled through the second exit needle and out of a patient body, the attached second hook-like grasper tool and the one or more third wire tools engaging a selected left lamina, the one or more third wire tools having a curved middle portion lying adjacent to the inferior aspect of the left lamina, the curved middle portion cuts the left lamina
of the target vertebra in an anterior to posterior direction
1460

Implementing a plurality of safety mechanisms that include an intraoperative electromyogram, one or more nerve conduction studies and one or more nerve sensors to achieve a safe percutaneous environment 1470.

Entering a first introducer epidural needle that includes a proximal end outside of the patient, a distal end, a first hollow internal diameter and a first penetrating perforating tip, the first penetrating perforating tip is disposed on the distal end, the first hollow internal diameter allows one or more first wire tools to pass through the first introducer epidural needle, the first penetrating perforating tip is percutaneously placed into an epidural space of a spine on a first side allowing the one or more first wire tools to be introduced and entered into the epidural space of a selected right lamina of the spine above a targeted vertebra with a side, where a spinous process divides a right lamina and a left lamina
1510

Entering a first exit epidural needle that includes a proximal end outside of the patient, a distal end, a second hollow internal diameter and a second penetrating perforating tip, the second penetrating perforating tip is disposed on the distal end, the second hollow internal diameter allows one or more second wire tools to pass through the exit epidural needle, the second penetrating perforating tip is percutaneously placed into the neuroforaminal space of the spine a selected one level above, one level below and at an adjacent level to the selected right lamina of a targeted vertebra, the second penetrating perforating tip introduces and enters the second wire tools into the neuroforminal space of the spine a selected one level above, one level below and at an adjacent level to the selected right lamina of a targeted lamina, the first penetrating perforating tip in the epidural space of a selected right lamina of the spine above a targeted vertebra with a side, where a spinous process divides a right lamina and a left lamina and the second penetrating perforating tip in the neuroforaminal space of the spine a selected one level above, one level below and at an adjacent level to the selected right lamina of a targeted vertebra resulting in the first penetrating perforating tip and the second penetrating perforating tip facing each other, the first penetrating perforating tip and the second penetrating perforating tip centering the neuroforaminal canal of the right side of the target vertebra
1520

A

Introducing a first hook-like grasper tool with a distal end and a proximal end outside of the patient, the distal end of the first hook-like grasper wire tool is a selected one of manually extended and mechanically extended through the first hollow internal diameter of the first exit epidural needle, the distal end of the first hook-like grasper tool attaches the one or more first wire tools introduced through the first introducer epidural needle within the neuroforaminal space of the spine a selected one level above, one level below and at an adjacent level to the selected right lamina of a targeted vertebra, the one or more first wire tools and the first hook-like grasper tool are pulled through the first exit epidural needle and out of a patient body, the one or more first wire tools having a curved middle portion, the curved middle portion lying adjacent to the neuroforamen and the neuroforaminal canal, the curved middle portion cuts one or more boney structures of the neuroforamen and the neuroforaminal canal
1530

Implementing a plurality of safety mechanisms that include an intraoperative electromyogram, a one or more nerve conduction studies and one or more nerve sensors to achieve a safe percutaneous environment
1540.

Figure 12B

PERCUTANEOUS METHODS FOR SPINAL STENOSIS AND FORAMINAL STENOSIS

This application is a Divisional application of U.S. non-provisional application Ser. No. 13/551,166 which claims priority to U.S. Provisional Application 61/508,999 filed on Jul. 18, 2011, the entire disclosure of each is incorporated by reference.

TECHNICAL FIELD & BACKGROUND

Spinal canal stenosis and foraminal stenosis are very common diseases of the spine affecting a relatively significant number of people involving all age groups. Spinal stenosis is a disease of the spinal column that is caused by a progressive narrowing of the spinal canal and/or neuroforaminal space thus limiting and restricting the space or room for neural elements. Canal stenosis can be due to the hypertrophy of both posterior elements and or anterior elements within the spinal canal. Canal stenosis can also occur due to overgrowth of bone tissue, ligamentum flavum, soft tissue or tumor inside the canal. Mostly a disease of the elderly, as life expectancy increases so does the incidence of spinal canal stenosis. In younger populations it can be seen with congenital anomalies such as associated canal stenosis secondary to short pedicles, trauma or other factors. As symptoms and disease progress the neural elements are compressed further typically resulting in pain, weakness, numbness, burning sensations, tingling and/or in severe cases can cause bladder and bowel instability, bladder or bowel failure and/or paralysis of the upper body and/or lower body depending on which levels of the spine are affected. Additionally, foraminal stenosis is a narrowing of the spinal foramen that pathologically compresses a spinal nerve as it exits the spine. Additionally, foraminal stenosis can be associated with central canal stenosis or can be an independent pathology.

The intervertebral foramen provides a protective exit tunnel for the spinal nerve to leave the spinal canal. The intervertebral foramen is formed posteriorly by the superior articular process of the vertebra below and the inferior articular process of the vertebra above, anteriorly by the vertebral bodies and the intervening intervertebral disc, and superiorly and inferiorly by the respective vertebral pedicles. Foraminal stenosis refers to narrowing of the intervertebral foramina. It is commonly caused by a degenerative articular process enlargement posteriorly, anteriorly by posterolateral intervertebral disc bulging and posterolateral vertebral body lipping (osteophytes), and superiorly by the vertebral pedicle that moves inferiorly with intervertebral disc dehydration and collapse during degenerative disc disease.

As the result of canal and or foraminal stenosis, nerves and/or spinal cord are compressed resulting in pain, tingling, numbness and weakness in the muscles of the affected area. Current medical practice regarding central stenosis and foraminal stenosis has afforded limited viable minimally invasive choices to both practitioners and patients. In mild cases, canal stenosis and foraminal stenosis can be treated with rest, rehabilitation, strengthening, oral analgesics, anti-inflammatory drugs and/or other conservative measures. Moderate cases can be treated temporarily with corticosteroids generally in the form of epidural steroid injections for canal stenosis or transforaminal epidural steroid injections for foraminal stenosis in combination with conservative measures typically with limited or mixed results. Open surgeries are reserved for progressive cases of foraminal stenosis and canal stenosis with variable results. Results depend on the cause of the patient's lower back pain and most patients can expect considerable relief from pain and some improvement in functioning. However there is some disagreement among surgeons about the success rate of open spine surgeries, which appears to be due to the several factors most notably failed back syndrome (scar tissue from post open surgery). Minimally invasive surgical procedures and devices have been developed over the years to treat spinal stenosis but with limited success. Typically these devices have only treated these symptoms by restricting movement and according to some reports with less than 50% of patients reporting some pain relief.

As surgical techniques, procedures and devices have progressed and improved the trend for less invasive and minimally invasive procedures and devices has become desired by both practitioners and patients. There are many benefits associated with minimally invasive procedures as seen in many surgical specialties and subspecialties including less invasive arthroscopic procedures, laparoscopic procedures and minimally invasive spinal procedures. Several newer spinal related surgical procedures claim to be minimally invasive but in actuality are open or partial open techniques and require general anesthesia and carry the same or similar intraoperative risks in regards to general anesthesia as general open procedures. This has been a major problem affecting both practitioners and patients in respect to the void of truly viable minimally invasive approaches to spinal stenosis and foraminal stenosis.

The present invention generally relates to a plurality of methods for treating one or more spinal conditions particularly for spinal stenosis, spinal compression, foraminal compression and foraminal stenosis that utilizes a plurality of exclusively percutaneous methods using a plurality of T-techniques. The T-techniques are minimally invasive techniques to treat spinal stenosis and foraminal stenosis. The present invention achieves decompression of the spinal canal and the neuroforamen through percutaneous techniques and methods where a cutting instrument or tissue modifying tool are in the form of a wire tool which is made to pass through an epidural needle tool (introducer needle) and made to exit through another epidural needle tool (exit needle) with the help of a grasper like tool such that the tissue modifying wire tool remains behind (inferior to) the target lamina or roof of the foramen while the two ends (a proximal and distal portion) of the tissue modifying wire tool remain outside the patient's skin. In carrying out the objectives of the T-techniques, several additional benefits will accompany these methods which include the use of a minimally invasive procedure and experience, minimal or no scar post-op, minimal or no bleeding during or post-op, minimal or no failed back surgery syndrome, minimal or no scar tissue, using a procedure being performed under local anesthesia with no added potential complications from general anesthesia, less pain following the procedure, less time in the operating room and less time spent in a recovery phase. Patients will be awake during the procedure and will be able to feel an immediate relief. As only a minimally invasive modification is used, mainly the diseased anatomy is manipulated and/or maneuvered thus allowing for a quicker and more natural healing.

The present invention results in less time spent in the hospital as compared to more invasive procedures especially for elderly or relatively more complicated cases and can be performed in an outpatient setting in younger patients or on a case by case basis. Unfortunately, as a person ages the risk of complications increase during prolonged intraoperative procedures under general anesthesia. The complications associated with general anesthesia are well known and documented. The present invention is unlike other procedures, techniques or devices that have preceded it in respect to spinal stenosis and foraminal stenosis in that it is the only procedure that provides a truly minimally invasive percutaneous laminoplasty or foraminoplasty that manipulates and corrects the diseased anatomy while the patient is awake and not under general anesthesia. Thus the complications inherent of general anesthesia are avoided. Furthermore, as the patient is awake during the procedure the possibility of getting a nerve injury is lessened and almost negligible as the patient will get paresthesia even with a slight touch of the wire tool with the spinal cord or a nerve root. The paresthesia is accepted as an initial safety gauge in many performed minimally invasive percutaneous spinal procedures today such as lumbar epidural injections, transforaminal epidural steroid injections and other similar procedures. The paresthesia allows a practitioner to know that he is in a sensitive area and to modify his or her approach. This is only possible if the patient is awake as in the present invention. Open techniques and/or partially open techniques do not have this level of safety because patients are under general anesthesia. Added measures of safety can be provided that also include patient feedback devices such as nerve stimulators, electromyography (EMG), evoked muscle action potentials, epiduroscopes and other commonly accepted methods for determining early injury to nerve or dura.

The present invention at its most basic description is the simple idea of passing a wire tool through two needle tools as described herein as the T-technique and method. The T-technique is a minimally invasive method for the treatment of spinal stenosis and foraminal stenosis. In the scope of medical practice there have been limited choices for both patients and physicians in regards to minimally invasive procedures for treatment of spinal stenosis and foraminal stenosis. The traditional methods of laminoplasty, laminectomy, foraminoplasty and other suitable methods of treatment are open procedures and carry the inherent risks of general anesthesia, prolonged operating time and other well-documented complications. An X-STOP™ titanium implant made by Medtronic Inc. is an implanted device that only treats symptomology mainly by restricting extension of the stenotic segment of the lumbar spine. The Baxano® technique or iO-FLEX™ system is described as a system that utilizes thin, flexible instruments to provide precision lumbar decompression from the "inside out". The Baxano® technique in practicality is an open or partially open technique that requires full general anesthesia and thus when examining the safety profile of the Baxano® technique the complications associated with general anesthesia must be included. In contrast, the present invention known as the T-technique is a truly percutaneous minimally invasive method for treating spinal stenosis and foraminal stenosis that is performed under local anesthesia that corrects and treats both pathology and symptomology.

The present invention described herein as the T-Technique is completely percutaneous and does not utilize open technique. This is unlike other techniques such as the Baxano Corporation technique where the exit of a surgical tool-like wire is not clear and/or is continuously pushed through tissue dangerously and is practically not possible and/or where exit cannot be possible without an open technique. The present invention utilizes the idea of percutaneously being able to connect one epidural space to another epidural space by passing any conjoining tool including a guide wire tool, a cutting tool, a hollow tube with a lumen capable of allowing additional guide wire tools to be passed through it, or any other suitable tissue modifying device or wire by using any tool or tools including a pair of epidural needles. Furthermore the T-Technique may be used in this method as described herein to connect one or multiple epidural interlaminar spaces with one or multiple other epidural interlaminar spaces at the same level and/or different levels of the spine.

The present invention utilizes the idea of percutaneously being able to connect one epidural space to an intervertebral foraminal space through passing any conjoining tool including a guide wire tool, a cutting tool, a hollow tube with a lumen capable of allowing additional guide wire tools to be passed through it, or any other suitable tissue modifying device or wire by using any tool or tools including a pair of epidural needles. Furthermore the T-Technique may be used in this method as described herein to connect one or multiple epidural interlaminar spaces with one or multiple other intervertebral foraminal spaces at the same level and/or different levels of the spine.

The present invention also utilizes the idea of percutaneously being able to connect from one intervertebral foraminal space to an other intervertebral foraminal space by passing any conjoining tool including a guide wire tool, a cutting tool, a hollow tube with a lumen capable of allowing additional guide wire tools to be passed through it, or any other suitable tissue modifying device or wire by using any tool or tools including a pair of epidural needles. Furthermore the T-Technique may be used in this method as described herein to connect one or multiple intervertebral foraminal spaces with one or multiple other intervertebral foraminal spaces at the same level and/or different levels of the spine.

The present invention can be performed for any combination of percutaneous laminoplasty and percutaneous foraminoplasty. The idea of a third needle tool, a fourth needle tool, a fifth needle tool and additional consecutive needle tools can be added on such that instead of using just (two) 2 epidural needle tools where the first would be an introducer needle tool and the second an exit needle tool, that some other combination of similar needle tools could perform the same function as utilized with the previously mentioned methods described herein. In regards to the term needle, it is defined as any tool or tools that are used to puncture or enter an epidural space or a neuroforaminal space through a percutaneous technique in contrast to open technique and as described for purposes and intentions herein described as the T-Technique. The T-Technique can include in its description the passing of any conjoining tool including a guide wire tool, a cutting tool, a hollow tube with a lumen capable of allowing additional guide wire tools to be passed through its lumen, or any other suitable tissue modifying device that can transport similar tools to connect interlaminar epidural spaces with other interlaminar epidural spaces and/or to connect interlaminar epidural spaces with intervertebral foraminal spaces and/or to connect intervertebral foraminal spaces with other intervertebral foraminal spaces using any suitable tool or tools including a pair of epidural needles. These needle tools will include an introducer and exit needle tool and can allow other medical tools such as forceps, graspers, wires and other medical tools to pass through the needle tools and be able to function and perform as a medical instrument, tool or device inside the patient's body in the epidural space or neuroforaminal space. A medical tool for example like a grasper tool can be used functionally to catch a guide wire tool that is passed through the introducer needle tool. Furthermore, other functions of the medical tools passed through the introducer or exit epidural needle tools inside the patient's body can include the ability to deliver medicines, irrigate fluids and suction fluids as well as the ability to maneuver and place other medical surgical tools and devices including surgical cutting wire and abrasive tissue modifying tools in desired target areas.

The present invention is a method performed percutaneously which will increase the anteroposterior (AP) diameter of the spinal canal for canal stenosis as well create increased foraminal space to relieve pressure on compressed exiting spinal nerves in foraminal stenosis. This resultant space creation and pressure relief of neural elements will be resultant of the abrasive and cutting nature of the percutaneous T-techniques and methods described herein. The T-technique's abrasive and cutting action applied to target segments of vertebral bone including lamina, spinous process, superior articular process, inferior articular process, pedicle and other desired target tissue will heal with or without percutaneous fusion though a natural healing process. A major benefit for a patient who experiences the percutaneous T-Technique for spinal stenosis or foraminal stenosis is decreased healing time as the adjacent structures will remain intact as compared to open and partially open techniques that require substantial tissue modification and dissection and thus prolonged healing times.

The present invention utilizes a plurality of T-technique methods that are percutaneous minimally invasive techniques that provide anatomical change in context to laminoplasty and foraminoplasty. The T-techniques do not require open technique or partially open technique as required by traditional laminoplasty or foraminoplasty. The T-technique for percutaneous laminoplasty will potentially replace a large portion of the open surgical methods in current practice by a simple percutaneous procedure for cutting lamina and other desired bones. Additionally the T-technique for percutaneous foraminoplasty will also potentially replace a large portion of the open surgical methods in current practice by a simple percutaneous procedure that allows for partial cutting through one or more superior and/or inferior articular processes and/or pedicle. This relief of pressure and space creating will cause the patient to feel a reduction of pain immediately following T-Technique. The present invention also includes a T-technique percutaneous laminoplasty with percutaneous foraminoplasty that is a combination of both previously described techniques herein. The T-techniques do not require any general anesthesia and can be completely done under local and or segmental regional anesthesia avoiding the risk of general anesthesia especially in an elderly population. The T-techniques can be used to treat radiculopathy and can be used to achieve decompression due to cord (neural ailment) compression, where the compression is due to one or more posterior overgrown structures. The T-techniques can be a procedure of choice for one or more syndromes where younger patients develop canal stenosis due to short pedicles and other congenital anomalies. Because of its simplicity and ease, the T-technique can give practitioners the ability to treat developing cases and earlier staged cases in canal and foraminal stenosis to avoid the complications of chronic disease. The T-technique will be used for central canal stenosis and for lateral canal stenosis (foraminal stenosis). The T-techniques may be a procedure of choice for all ages especially patients categorized as high risk for intraoperative procedures. The technical aspects of performing the described T-technique will be no more difficult than that of procedures performed in common pain management practice today. The percutaneous T-Technique will provide a patient with desired modification of the diseased anatomical structures including ligamentum flavum, pedicle, lamina and articular processes. This will occur by application of the present invention's cutting and abrasive properties, and subsequent stretching, pulling and mobilizing of loose bone followed by stabilization and natural boney healing with fusion resulting in an increase of space for neural elements and pain relief.

The present invention will increase AP diameter of the spinal canal by a percutaneous (through the skin) procedure that does not require vertical or horizontal incisions as do traditional open surgeries such as laminectomy, laminoplasty, foraminoplasty and foraminotomy. This incision for traditional open surgeries has to be made through many layers of tissue including skin, fat and muscle that must be dissected and retracted. The trauma inflicted to the muscle and surrounding tissue requires significant time to heal after surgery. Because this is a percutaneous technique there are no long incisions during T-technique. Practitioners do not have to cut through muscle or surrounding tissue to complete the procedure, leading to less tissue damage and quicker recovery. The present invention is a percutaneous technique described for laminoplasty and foraminoplasty patients that will experience minimal or no scarring of skin as well as less or negligible scar tissue and surgical adhesions which is a common cause of failed back syndrome related to open techniques.

The T-techniques can be performed in a more efficient and safer manner when compared to open procedures resulting in less time in the operating room for the patient. The patient will not have to undergo general anesthesia as the T-technique is performed under local anesthesia, thus avoiding the risks and complications that accompany general anesthesia. Under the T-techniques there will be less blood loss as compared to traditional open techniques. The patient will suffer less pain with the T-techniques when compared to traditional open surgeries. The T-techniques can reduce the overall hospital stay and T-technique patients will be able to start mobilization earlier than patients that have traditional open technique methods. The present invention is a minimally invasive procedure with minimal or no bleeding during procedure or post-op, minimal or no failed back surgery incidence (scar tissue) and is performed under local anesthesia without added complications from general anesthesia. The present invention involves less pain following the procedure, less time in an operating room, less time spent in the recovery phase and patients will be awake during the procedure and will be able to feel relative immediate relief. As only a minimally invasive modification is used, mainly the diseased anatomy is maneuvered thus allowing for a relative quicker and more natural healing process. The present invention also allows for less time spent in the hospital and can be performed in an outpatient setting on relatively younger patients or on a case by case basis.

BRIEF DESCRIPTION OF THE DRAWINGS

The present invention will be described by way of exemplary embodiments, but not limitations, illustrated in the accompanying drawings in which like references denote similar elements, and in which:

FIGS. 11A, 11B, 11C and 11D illustrate a flowchart of a method for performing a percutaneous laminoplasty, in accordance with one embodiment of the present invention.

FIGS. 12A and 12B illustrate a flowchart of a method 1500 for performing a percutaneous foraminoplasty, in accordance with one embodiment of the present invention.

DETAILED DESCRIPTION OF ILLUSTRATIVE EMBODIMENTS

Various aspects of the illustrative embodiments will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative embodiments. However, it will be apparent to one skilled in the art that the present invention may be practiced without the specific details. In other instances, well-known features are omitted or simplified in order not to obscure the illustrative embodiments.

Various operations will be described as multiple discrete operations, in turn, in a manner that is most helpful in understanding the present invention. However, the order of description should not be construed as to imply that these operations are necessarily order dependent. In particular, these operations need not be performed in the order of presentation.

The phrase in one embodiment is utilized repeatedly. The phrase generally does not refer to the same embodiment, however, it may. The terms comprising, having and including are synonymous, unless the context dictates otherwise.

Figure 1:
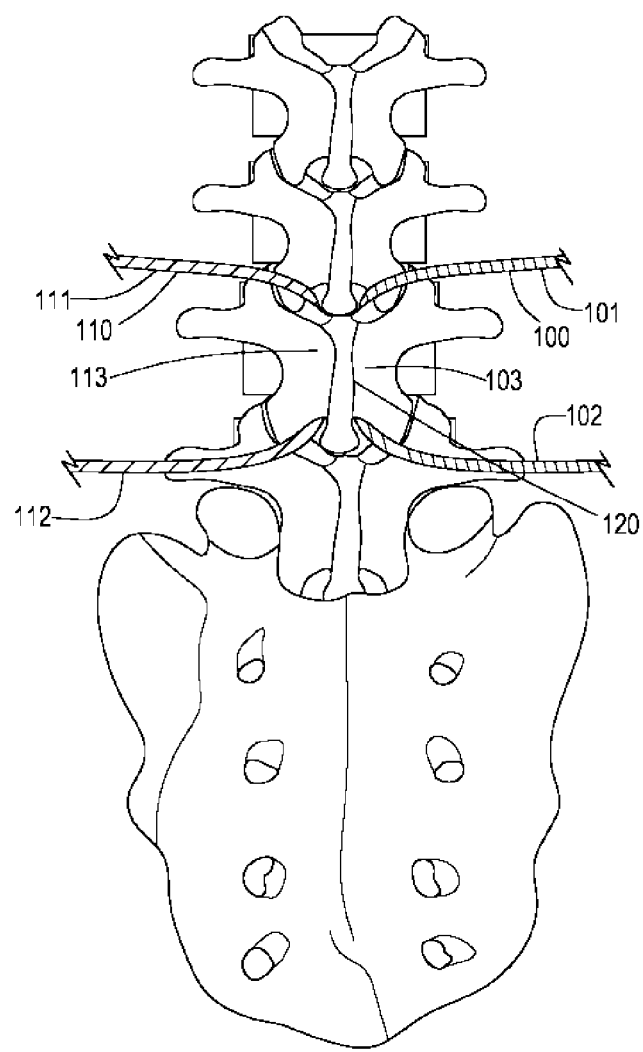
FIG. 1 is a front perspective view of a cutting wire utilized during cutting of a lamina on a left side or a right side of a spinous process, in accordance with one embodiment of the present invention.

FIG. 1 is a front perspective view of a pair of cutting wires performing percutaneous laminoplasty by T-Technique. The left cutting wire 110 is on the left side of the body and lies to the left of the spinous process 120 inferior to the left L5 lamina 113. The right cutting wire 100 is on the right side of the body and lies to the right of the spinous process 120 inferior to the right L5 lamina 103. The right cutting wire 100 is on the right side of the body and lies to the right of the spinous process 120 and has a proximal end 101 and a distal end 102 that are illustrated in FIG. 1 outside of the body. The left cutting wire 110 on the left side has a proximal end 111 and a distal end 112 that are illustrated in FIG. 1 outside of the body.

Figure 2:
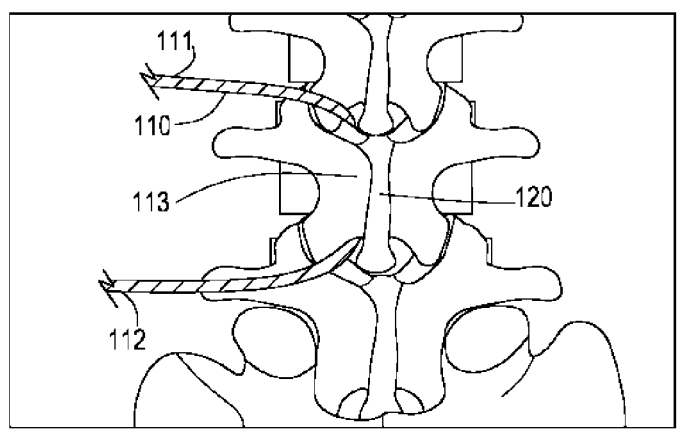
FIG. 2 is a front perspective view of a metallic wire utilized during cutting a left lamina on a left side of a spinous process, in accordance with one embodiment of the present invention.

FIG. 2 is a front perspective view of a left cutting wire 110 with a proximal end 111 and a distal end 112 utilized during a percutaneous laminoplasty by a T-technique process, in accordance with one embodiment of the present invention. The left cutting wire 110 is positioned across the left side of L5 Lamina 113 on left side of spinous process 120. The proximal end 111 and distal end 112 of the left cutting wire 110 remain outside of the body.

Figure 3:
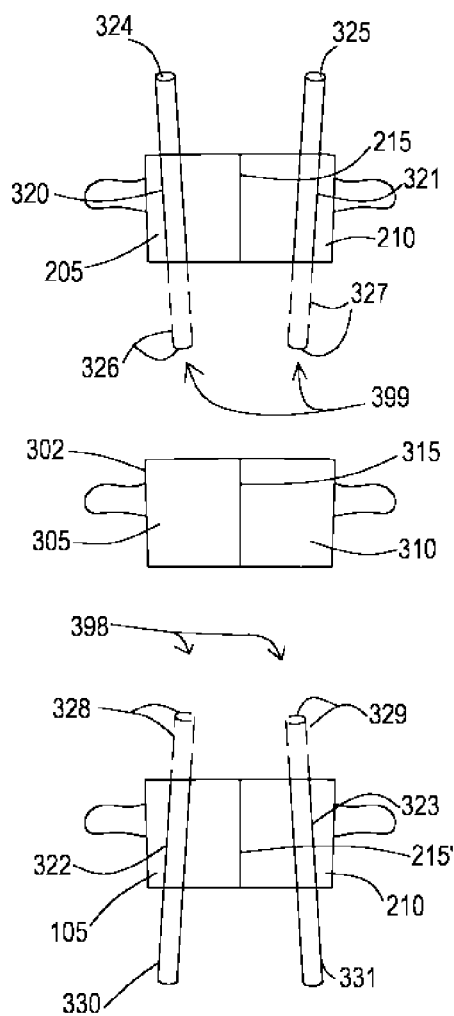
FIG. 3 is a front view of 4 needles in two epidural spaces keeping a target lamina in a center area, in accordance with one embodiment of the present invention.

FIG. 3 is a front view of 4 needles in two epidural spaces keeping a target lamina in a center area, in accordance with one embodiment of the present invention.

FIG. 3 includes a left lamina 305, a right lamina 310 and a spinous process 315 which divides the right lamina 310 and the left lamina 305 of the target vertebra 302. FIG. 3 also includes a left lamina 205, a spinous process 215 and a right lamina 210 of a vertebra one level above target vertebra 302. FIG. 3 also demonstrates left lamina 105, spinous process 215' and right lamina 210' of the vertebra one level below target vertebra 302. FIG. 3 also illustrates a left introducer epidural needle 320, a right introducer epidural needle 321, a left exit epidural needle 322 and a right exit epidural needle 323. The left introducer needle 320 has a proximal end 324 and a distal end 326. The right introducer needle 321 has a proximal end 325 and a distal end 327. The left exit needle 322 has a proximal end 330 and a distal end 328. The right exit needle 323 has a proximal end 331 and a distal end 329. The proximal ends of introducer needles 324, 325 and the proximal ends of the exit needles 330, 331 remain outside of the patient's body. The distal ends of the introducer needles 326, 327 enter the epidural space 399 above target vertebra 302. The distal ends of the exit needles 328, 329 enter the epidural space 398 below the target vertebra 302.

The left introducer needle 320 and its distal end 326 is placed and introduced in the epidural space 399 above the target vertebra 302 to the left of the spinous process 315. The right introducer needle 321 and its distal end 327 are introduced in epidural space 399 on the right side of spinous process 315. The left exit epidural needle 322 and its distal end 328 enter the epidural space 398 below target vertebra 302 to the left of the spinous process 315. The right exit needle 323 and its distal end 329 enter the epidural space 398 below target vertebra 302 to the left of the spinous process 315. FIG. 3 illustrates that the left distal end 326 of the introducer needle 320 and the left distal end 328 of the exit needle 322 are facing each other. FIG. 3 further illustrates that the right distal end 327 of the introducer needle 321 and the right distal end 329 of the exit needle 323 are facing each other.

Figure 4:
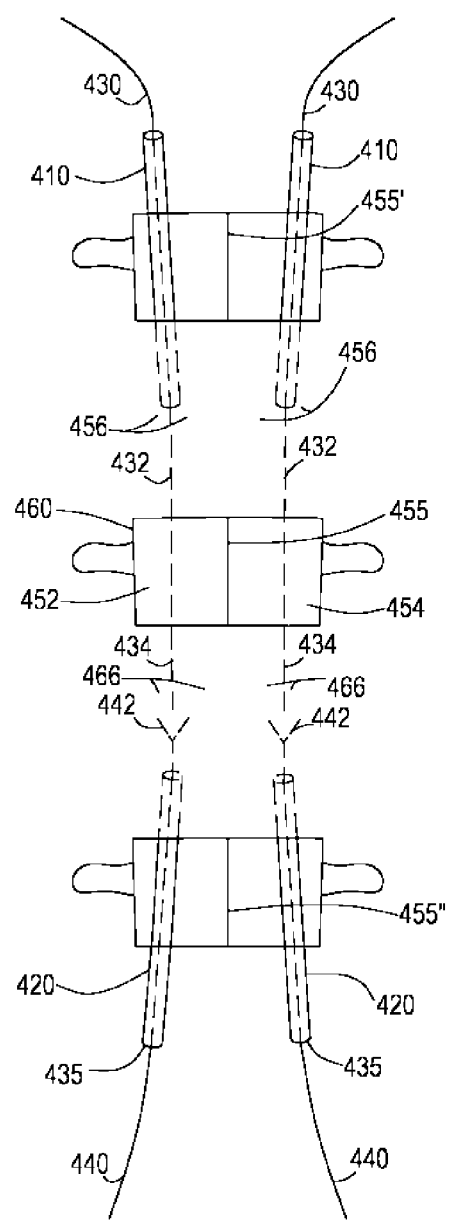
FIG. 4 is a front view of 4 needles with a pair of cutting wires and a pair of graspers, in accordance with one embodiment of the present invention.

FIG. 4 is a front view of 4 needles with a pair of cutting wires and a pair of graspers, in accordance with one embodiment of the present invention. FIG. 4 includes a pair of introducer needles 410, a pair of exit needles 420, a pair of cutting wires 430, a pair of grasper tools 440, a left lamina 452 of target vertebra 460 and a right lamina 454 of target vertebra 460, a spinous process 455 of target vertebra 460, a spinous process 455' of vertebra one level above target vertebra and a spinous process 455" of vertebra one level below target vertebra, a pair of distal ends 442 of the pair of grasper tools 440, a pair of traversing distal ends 432 of the pair of cutting wires 430 through an epidural space and a pair of distal ends 434 of the pair of cutting wires 430 through a target vertebra 460.

Illustrating T-technique percutaneous laminoplasty is done through FIG. 4. A pair of exit epidural needles 420 and a pair of introducer epidural needles 410 are illustrated in FIG. 4. The left introducer epidural needle 410 distal end will enter into the epidural space 456 above target vertebra 460 to left of spinous process 455. The right introducer epidural needle 410 distal end will enter into the epidural space 456 above target vertebra 460 to right of spinous process 455. The left exit needle 420 distal end will enter the epidural space 466 below target vertebra 460 to the left of the spinous process 455. The right exit needle 420 distal end will enter the epidural space 466 below target vertebra 460 to the right of the spinous process 455.

The pair of cutting wires 430 is passed through and exits the pair of introducer epidural needles 410 and enters the epidural space 456 on each respective side of the spinous process 455. The left cutting wire 430 can be any suitable tissue modifying wire and is pushed manually or with the aid of a mechanical or electronic device through the distal end of the left introducer epidural needle 410 to cross through the epidural space 456 and go behind (inferior to) the left target lamina 452 on left side of spinous process 455. Similarly the right cutting wire 430 can be any suitable tissue modifying wire and is pushed manually or with the aid of a mechanic or electronic device through the distal end of the right introducer needle 410 to cross through the epidural space 456 and go behind (inferior to) the right target lamina 454 on right side of spinous process 455. The cutting wire 430 (which is one continuous wire) as described and illustrated in FIG. 4 as having a proximal end 430 (outside of the body that enters introducer epidural needle 410), a middle part 432 (describes the part of the cutting wire 430 that is immediately exiting the introducer epidural needle 410 inside epidural space 456 and continuing to reach the epidural space 466 one level below) and at this position in the T-technique is labeled as the distal end of the guide wire 434. (In subsequent stages of T-technique the distal end of the guide wire 434 will be located outside of the body.)

The grasper tool 440 (the proximal end that is outside the body) is introduced through the pair of exit needles 420. The distal end of the grasper 442 is illustrated in FIG. 4 and is seen immediately exiting the exit needle and placed in the epidural space 466. The distal ends of the grasper tool 442 will catch the distal ends of wire 434 in the epidural space 466. The distal portion of the grasper 442 now controlling the distal portion of the cutting wire 434 will proceed to exit the epidural space and retreat in the opposite direction from which it came from to exit the body though the exit needle 420 and pull the distal wire 434 it has captured out through the exit needles 420. The distal end of the cutting wire 435 is seen once it has exited the body after being pulled by the grasper tool 440 through the exit needle 420.

Figure 5:
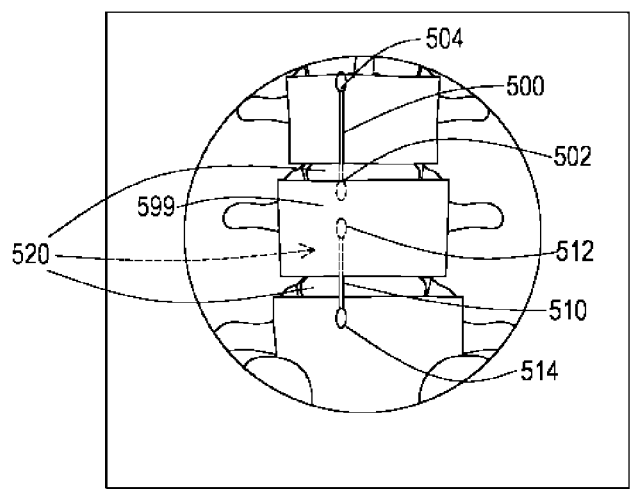
FIG. 5 is a front view of an exit needle and an introducer needle in an epidural space on a left side of a spinous process targeting a L5 lamina, in accordance with one embodiment of the present invention.

FIG. 5 is a front perspective view of an exit needle 500 and an introducer needle 510 in an epidural space 520 under target vertebra 599, in accordance with one embodiment of the present invention. The exit needle 500 has a distal tip 502 and a proximal head 504 and the introducer needle 510 has a distal tip 512 and a proximal head 514 as well. The distal tips 502, 512 point toward and face each other allowing a grasping tool (not shown) that is passed through the exit needle 500 that will catch a guide wire (not shown) in the epidural space 520. The guide wire will be passed through an introducer needle 510. The grasping tool will pull the guide wire out through the exit needle 500.

Figure 6:
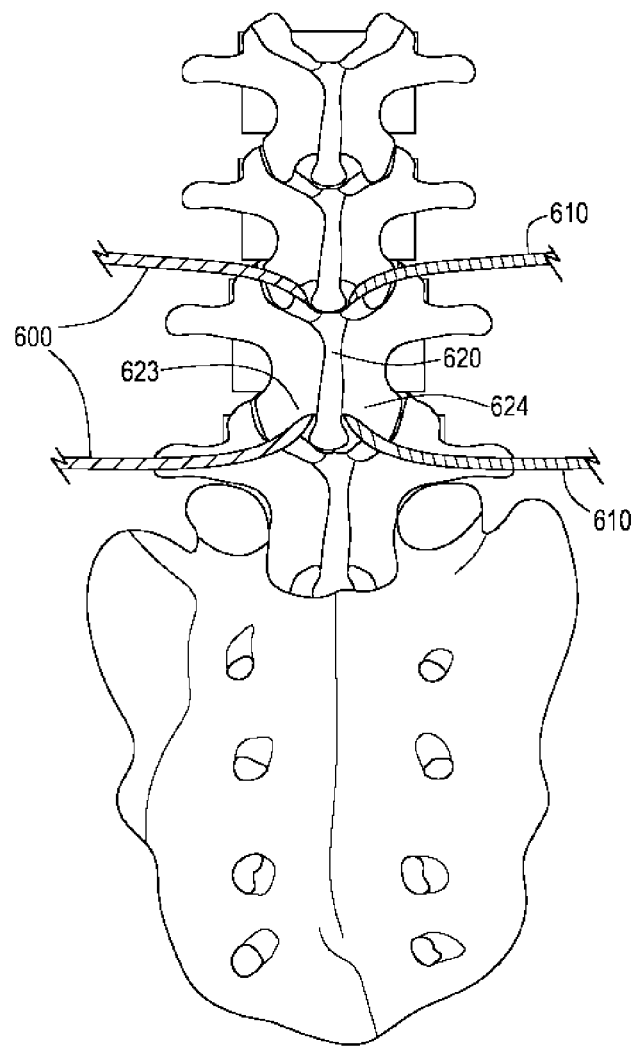
FIG. 6 is a front perspective view of a pair of wires cutting a lamina on a left side and a right side of a spinous process during a percutaneous laminoplasty by a T-technique, in accordance with one embodiment of the present invention.

FIG. 6 is a front perspective view of a pair of guide wires illustrating a percutaneous laminoplasty by T-technique, in accordance with one embodiment of the present invention. The pair of guide wires includes a left guide wire 600 and a right guide wire 610. The left guide wire 600 is a bone cutting wire placed inferior to (behind) the left lamina 623 to the left of the spinous process 620. The right guide wire 610 is a bone cutting wire placed inferior to (behind) the right lamina 624 to the right of the spinous process 620. The left guide wire 600 and the right guide wire 610 are inserted through the patient's body having a proximal end and distal end that extend outside of the patient's body. The left guide wire 600 and the right guide wire 610 can be utilized on any vertebrae along a patient's spinal column. Cutting motion or abrasive action is commenced as the distal ends and proximal ends of the left guide wire 600 and the right guide wire 610 are pushed and pulled with tension, force and/or vibration as the target tissue (right lamina 624 and left lamina 623) are cut in an abrasive manner from an anterior to a posterior direction (inside to out) on both sides of spinous process 620 through percutaneous method.

Figure 7:
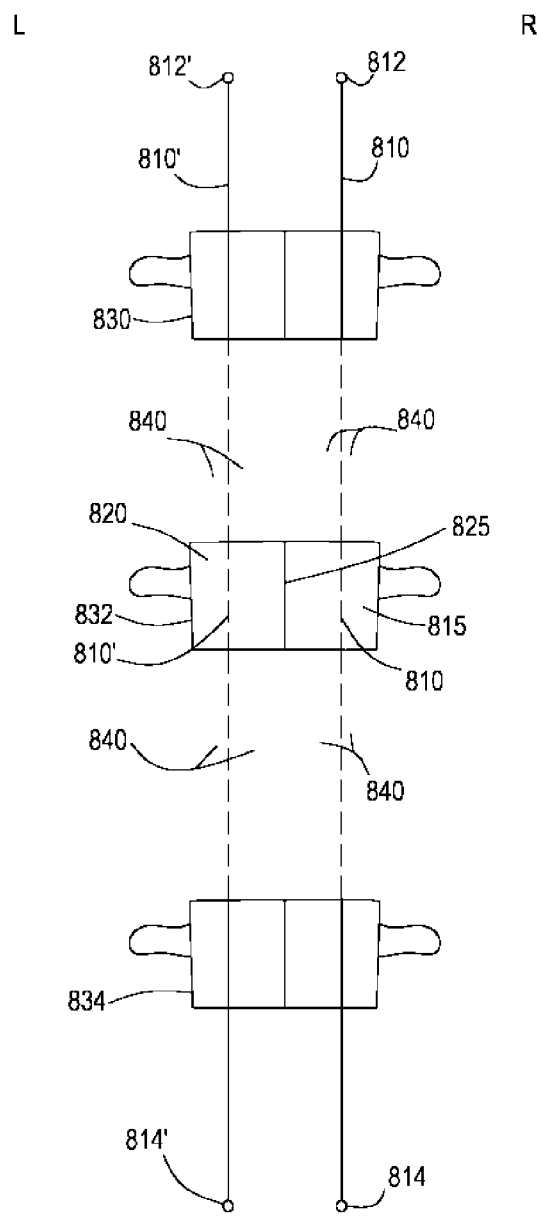
FIG. 7 is a front view of two cutting wires placed under a right target lamina and a left target lamina through an epidural space, in accordance with one embodiment of the present invention.

FIG. 7 is front perspective view of a right cutting wire and a left cutting wire in a final position behind a target lamina performing a percutaneous laminoplasty by a T-technique, in accordance with one embodiment of the present invention.

FIG. 7 includes a right cutting or tissue modifying wire 810 with a proximal end 812 located outside of the patient's body and a distal end 814 located outside of the patient's body. FIG. 7 demonstrates a desired positioning of the guide wire 810, 810' in accordance with the steps and methods described herein as the T-technique. The left guide wire 810' in a desired position behind (inferior) to left lamina 820 in relation to spinous process 825 and the right guide wire 810 in a desired position (inferior) to right lamina 815 in relation to spinous process 825. FIG. 7 also includes a left cutting or tissue modifying wire 810' with a proximal end 812' located outside of the patient's body and a distal end 814' also located outside of the patient's body. Three vertebrae bodies are illustrated in FIG. 7 including the target vertebra 832. A first vertebra 830 not involved in cutting is above target vertebra 832 and a second vertebra 834 not involved in cutting is below target vertebra 832. The connecting epidural space 840 extends above and below the target vertebra 832. Dotted lines of left cutting wire 810' illustrate the left cutting wire 810' to be in a desired cutting position lying adjacent to the inferior aspect of left target lamina 820 to the left of the spinous process 825. Dotted lines of right cutting wire 810 illustrate the right cutting wire 810 to be in a desired cutting position lying adjacent to the inferior aspect of right target lamina 815 to the right of the spinous process 825.

Figure 8:
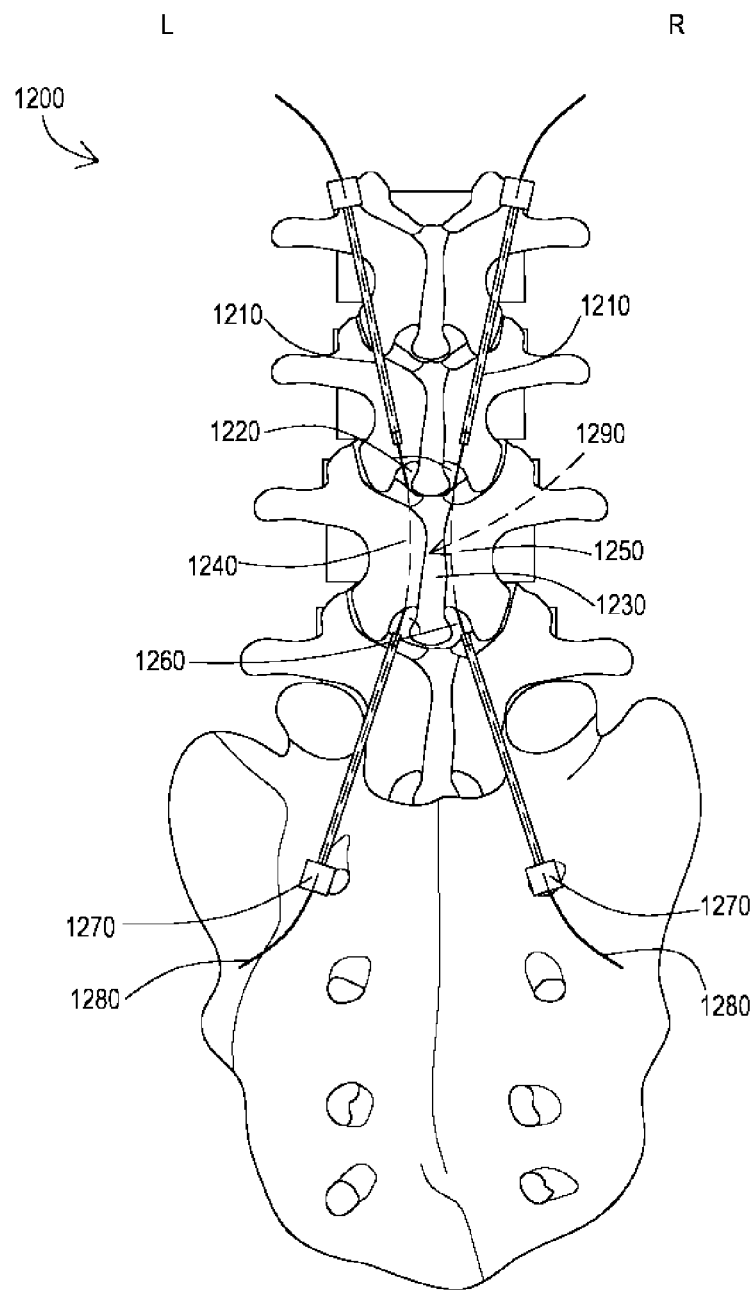
FIG. 8 is a front view model of a patient's spine that includes a pair of interchangeable exit needles and a pair of introducer needles, in accordance with one embodiment of the present invention.

FIG. 8 is a front view model of a patient's spine 1200 that includes a pair of interchangeable exit needles and a pair of introducer needles, in accordance with one embodiment of the present invention.

FIG. 8 includes a pair of exit needles 1210, a first epidural space 1220, a spinous process 1230, a left target lamina 1240, a right target lamina 1250, a second epidural space 1260, a pair of introducer needles 1270 and a pair of thread wire 1280.

The pair of exit needles 1210 and the pair of introducer needles 1270 are interchangeable. The pair of thread wire 1280 is passed through the pair of introducer needles 1270 and exits from the pair of exit needles 1210 such that the pair of thread wire 1280 remains behind (inferior to) the right target lamina 1250 and left target lamina 1240 on either side of the spinous process 1230.

The pair of exit needles 1210 and the pair of introducer needles 1270 are removed leaving the pair of thread wires 1280 in respective desired positions behind the target lamina 1240, 1250 with applied tension and pressure are moved back and forth resulting in a cutting motion from inside out through the right target lamina 1250 and the left target lamina 1240 thereby relieving pressure on a plurality of underlying neural tissue 1290 (not visibly seen in this diagram).

Figure 9:
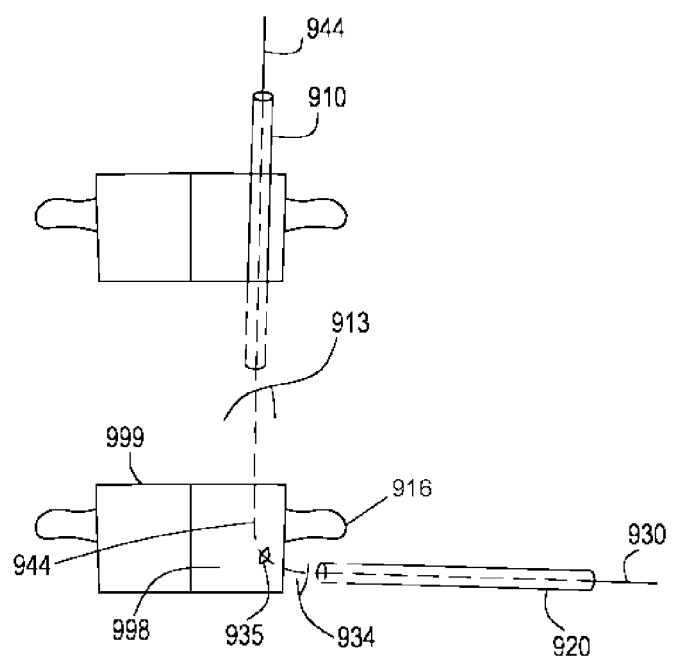
FIG. 9 illustrates a front view of a percutaneous foraminoplasty through a T-technique using an introducer interlaminar epidural needle tool and an exit needle tool in a neuroforaminal space, in accordance with one embodiment of the present invention.

FIG. 9 is a front view of a right sided percutaneous foraminoplasty performed by T-technique, where an introducer epidural needle is placed in an epidural space and an exit needle is placed in a neuroforaminal space, in accordance with one embodiment of the present invention.

FIG. 9 illustrates a percutaneous foraminoplasty that includes an introducer epidural needle 910, an exit needle 920, a proximal end of a catcher or forceps tool 930, a guide wire 944 (dotted lines) made of cutting wire or abrasive material, a right transverse process 916, a right lamina 999 of target vertebra 998 and a distal end 935 of the grasper tool 930 that is able to catch and secure the guide wire 944 in either an epidural space 913 or a neuroforaminal space 934. Once the distal end 935 of grasper tool 930 secures the guide wire 944, the grasper tool 930 will reverse and exit the exit needle 920 and pull the guide wire 944 with it outside the patient's body.

Figure 10:
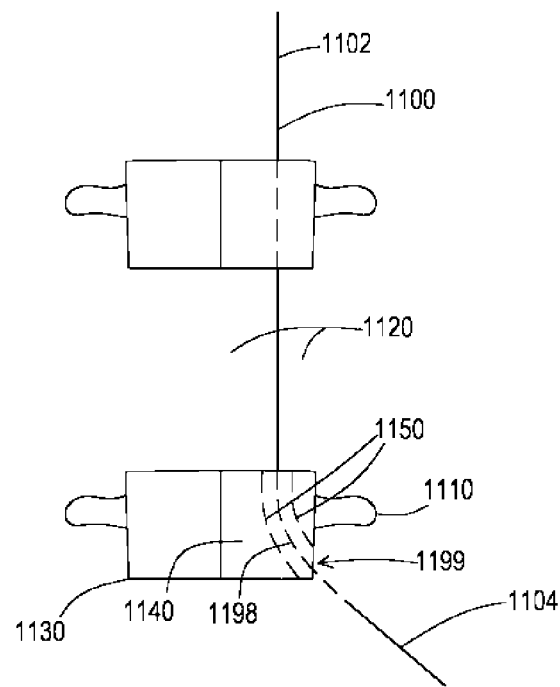
FIG. 10 is front view of a final position of a cutting wire after a plurality of needles are removed in a right side percutaneous foraminoplasty, in accordance with one embodiment of the present invention.
Figure 10:
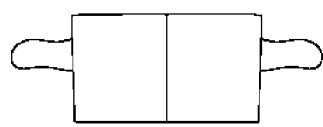

FIG. 10 is front view of a final position of a cutting wire or an abrasive wire 1100 after a plurality of needles (not shown) are removed in a right side percutaneous foraminoplasty, in accordance with one embodiment of the present invention. FIG. 10 illustrates the cutting or the abrasive wire 1100 in a final position after a pair of introducer needles (not shown) and the exit needles (not shown) are taken out.

The percutaneous foraminoplasty illustrated in FIG. 10 has the cutting wire or the abrasive wire 1100 that includes a proximal end 1102 (located outside of body) and a distal end 1104 (located outside of body). FIG. 10 also illustrates a right transverse process 1110, an epidural space 1120, a target vertebra 1130 possessing a neuroforaminal space 1199, a right lamina 1140 and a target tissue 1150 (shaded area) including right superior articular process (not shown) and right inferior articular process (not shown) and neuroforaminal canal (not shown). The cutting wire or the abrasive wire 1100 having a proximal end 1102 (located outside the patient's body) a distal end 1104 of the cutting wire or the abrasive wire 1100 (located outside the patient's body) and the middle portion 1198 adjacent to target tissue 1150 (shaded area) including right superior articular process (not shown) and right inferior articular process (not shown) and right neuroforaminal canal (not shown). The distal ends 1104 and proximal ends 1102 of the cutting and the abrasive wire 1100 has tension applied in a pulling and pushing motion that is either manually or electronically controlled with the middle portion 1198 of the cutting or the abrasive wire 1100 lying adjacent to target tissue 1150 (shaded area) including right superior articular process (not shown) and right inferior articular process (not shown) and right neuroforaminal canal (not shown).

FIGS. 11A, 11B, 11C and 11D illustrate a flowchart of a method 1400 for performing a percutaneous laminoplasty, in accordance with one embodiment of the present invention. The method 1400 for performing percutaneous laminoplasty utilizes a selected one of a local anesthesia and a segmental anesthesia while a patient is awake and in a prone position.

The steps of the method 1400 include entering a first introducer epidural needle that includes a proximal end outside of the patient, a distal end, a first hollow internal diameter and a first penetrating perforating tip, the first penetrating perforating tip is disposed on the distal end, the first hollow internal diameter allows one or more first wire tools to pass through the introducer epidural needle, the first penetrating perforating tip is percutaneously placed into an epidural space of a spine on a first side allowing the one or more first wire tools to be introduced and entered into the epidural space of a selected right lamina of the spine above a targeted vertebra with a side, where a spinous process divides a right lamina and a left lamina of the target vertebra 1410, entering a first exit epidural needle that includes a proximal end outside of the patient, a distal end, a second hollow internal diameter and a second penetrating perforating tip, the second penetrating perforating tip is disposed on the distal end, the second hollow internal diameter allows a one or more second wire tools to pass through the exit epidural needle, the second penetrating perforating tip is percutaneously placed into the epidural space of the spine that introduces and enters the second wire tools below the selected right lamina of the side of the targeted vertebra where the first introducer epidural needle is entered in the epidural space of the spine below the selected right lamina, the first penetrating perforating tip and the second penetrating perforating tip in the epidural space resulting in the first penetrating perforating tip and the second penetrating perforating tip facing each other, the first penetrating perforating tip and the second penetrating perforating tip centering the right lamina 1420, introducing a first hook-like grasper tool with a distal end and a proximal end outside of the patient, the distal end of the first hook-like grasper tool is a selected one of manually extended and mechanically extended through the first hollow internal diameter of the first exit epidural needle, the distal end of the first hook-like grasper tool attaches the one or more first wire tools introduced through the first introducer epidural needle within the epidural space, the one or more first wire tools and the first hook-like grasper tool are pulled through the first exit epidural needle and out of a patient body, the attached first hook-like grasper tool and the one or more first wire tools engaging below the selected right lamina of the target vertebra, where a spinous process divides the right lamina and the left lamina, the one or more first wire tools having a curved middle portion, the curved middle portion lying adjacent to the inferior aspect (behind) of right lamina, the curved middle portion cuts the right lamina of the target vertebra in an anterior to posterior direction 1430, entering a second introducer epidural needle that includes a proximal end outside of the patient, a distal end, a third hollow internal diameter and a third penetrating perforating tip disposed on the distal end, the third hollow internal diameter allows one or more third wire tools to pass through the second introducer epidural needle, the third penetrating perforating tip is percutaneously placed into the epidural space of the spine allowing the one or more third wire tools to be introduced and entered into the epidural space of a selected left lamina of the spine above a targeted vertebra with a side, where a spinous process divides the right lamina and the left lamina 1440, entering a second exit epidural needle that includes a proximal end outside of the patient, a distal end, a fourth hollow internal diameter, a fourth penetrating perforating tip disposed on the distal end that is a selected one of manually extended and mechanically extended, the fourth hollow internal diameter allows a selected one or more fourth wire tools to pass through the second exit epidural needle, the fourth penetrating perforating tip is percutaneously placed into the epidural space of the spine that introduces and enters the one or more fourth wire tools below the side of the targeted vertebra where the second introducer epidural needle is entered into the epidural space of the spine of the selected left lamina, the third penetrating perforating tip and the fourth penetrating perforating tip in the epidural space resulting in the third penetrating perforating tip and the fourth penetrating perforating tip facing each other, the third penetrating perforating tip and the fourth penetrating perforating tip centering the left lamina 1450, introducing a second hook-like grasper tool with a distal end and a proximal end outside of the patient, the distal end of the second hook-like grasper tool is a selected one of manually extended and mechanically extended through the fourth hollow internal diameter of the second exit epidural needle, the second hook-like grasper tool attaches the selected one or more third wire tools introduced through the second introducer epidural needle within the epidural space, the selected one or more third wire tools is pulled through the second exit needle and out of a patient body, the attached second hook-like grasper tool and the one or more third wire tools engaging a selected left lamina, the one or more third wire tools having a curved middle portion lying adjacent to the inferior aspect (behind) of left lamina, the curved middle portion cuts the left lamina of the target vertebra in an anterior to posterior direction 1460 and implementing a plurality of safety mechanisms that include an intraoperative electromyogram, a plurality of nerve conduction studies and one or more nerve sensors to achieve a safe percutaneous environment 1470.

The third hollow internal diameter allows a selected one or more first fluids and first medicines to pass through the second introducer epidural needle. The fourth hollow internal diameter allows a selected one or more second fluids and second medicines to pass through the second exit epidural needle. The introducer epidural needles are a selected one of a flat tipped introducer epidural needle, a curved introducer epidural needle, a rigid introducer epidural needle, a c-shaped introducer epidural needle, an expandable introducer epidural needle and a flexible introducer epidural needle. The introducer epidural needles have a selected one of a curved penetrating perforating tip and a penetrating perforating straight tip. The introducer epidural needles have a hollow tube that is a protective sheath. The one or more wire tools are a selected one from the group of a guide wire, a thread wire, a bone temperature sensor and a twisted wire. The one or more wire tools are made of a selected one of metal, plastic, nylon and rubber. The one or more wire tools have a selected one of bone cutting and one or more abrasive properties that spare nerves and dura when cutting. The one or more wire tools are utilized to modify tissue, to cut tissue and to cut bone. The one or more wire tools are a selected one of one or more bone-cutting devices, one or more t-saw (Tomita saw) wires, one or more bone cutting wires and a saw device. The one or more wire tools includes an expanding hollow lumen that allows one or more wires, fluids, and medical devices to pass through the expanding hollow lumen. The one or more wire tools includes a plurality of channels and a plurality of apertures to be passed through the expanding hollow lumen to irrigate one or more anatomical areas of the spine. The one or more anatomical areas of the spine are irrigated with cold water. The expanding hollow lumen is made of a selected one of a plastic and a malleable polymer. The one or more wire tools can provide suction. The one or more wire tools are a selected one of left in the epidural space, removed immediately from the epidural space and removed at a later date from the epidural space. The one or more wire tools have a plurality of grooves that pick-up bone debris osteophytes and carry the bone debris osteophytes outside the patient's body by a selected one of pushing and pulling of the one or more wire tools. The one or more wire tools can be an expanding balloon. The expanding balloon is a selected one of radio-opaque and radiolucent, the expanding balloon provides a larger target to the exit epidural needle. The one or more wire tools are a selected one of a plurality of pieces and one continuous piece. The one or more wire tools are a selected one of radiolucent and radiopaque. The one or more wire tools are a selected one or more of being magnetic, having one or more electromagnetic capabilities, generating heat, being coupled to a medical device that has a laser eliciting capability, producing a laser, being motorized, vibrating independently and vibrating at one or more calculated rhythms. The epiduroscope has an ultrasound guided capability and a wireless capability to transmit data. The hook-like grasper tools is a pair of grasping forceps. The hook-like grasper tools is a selected one or more of having a fork-shape, having one or more apertures, having a locking device, having a selected one of a closing door and a pinching door, having a sticky substance and having a selected one of magnetic properties and electromagnetic properties. The hook-like grasper tools can suture a selected one of a wire, a lead and a tool at more than one level along the spinal cord accommodates a pain pump lead and accommodates a spinal cord stimulator lead. The hook-like grasper tools attaches a selected one or more of one or more wires, leads, medical devices and desired target tissue by using a selected one of suture wire, one or more buttons, one or more bolsters, one or more bridges and thread. The method is replicated on one or more spinal cord levels that include cervical, thoracic, lumbar and sacral regions on the patient body. The method is performed under a selected one of X-Ray, fluoroscopy, ultrasound, CT, MRI, and 3D-MRI. In the method, the spinous process is cut to replace a selected one of the left lamina and the right lamina.

FIGS. 12A and 12B illustrate a flowchart of a method 1500 for performing a percutaneous foraminoplasty, in accordance with one embodiment of the present invention. The method 1500 for performing percutaneous foraminoplasty that utilizes a selected one of a local anesthesia and a segmental anesthesia while a patient is awake and in a prone position, the method for performing percutaneous laminoplasty is performed on a selected one of a first side and a second side of a spine.

The method 1500 comprises the steps of entering a first introducer epidural needle that includes a proximal end outside of the patient, a distal end, a first hollow internal diameter and a first penetrating perforating tip, the first penetrating perforating tip is disposed on the distal end, the first hollow internal diameter allows one or more first wire tools to pass through the first introducer epidural needle, the first penetrating perforating tip is percutaneously placed into the epidural space of a spine on a first side allowing the one or more first wire tools to be introduced and entered into the epidural space of a selected right lamina of the spine above a targeted vertebra with a side, where a spinous process divides a right lamina and a left lamina 1510, entering a first exit epidural needle that includes a proximal end outside of the patient, a distal end, a second hollow internal diameter and a second penetrating perforating tip, the second penetrating perforating tip is disposed on the distal end, the second hollow internal diameter allows one or more second wire tools to pass through the exit epidural needle, the second penetrating perforating tip is percutaneously placed into the neuroforaminal space of the spine a selected one level above, one level below and at an adjacent level to the selected right lamina of a targeted vertebra, the second penetrating perforating tip introduces and enters the second wire tools into the neuroforaminal space of the spine a selected one level above, one level below and at an adjacent level to the selected right lamina of a targeted vertebra, the first penetrating perforating tip in the epidural space of a selected right lamina of the spine above a targeted vertebra with a side, where a spinous process divides a right lamina and left lamina and the second penetrating perforating tip in the neuroforaminal space of the spine a selected one level above, one level below and at an adjacent level to the selected right lamina of a targeted vertebra, resulting in the first penetrating perforating tip and the second penetrating perforating tip facing each other, the first penetrating perforating tip and the second penetrating perforating tip centering the neuroforaminal canal of the right side of the target vertebra 1520, introducing a first hook-like grasper tool with a distal end and a proximal end outside of the patient, the distal end of the first hook-like grasper tool is a selected one of manually extended and mechanically extended through the first hollow internal diameter of the first exit epidural needle, the distal end of the first hook-like grasper wire tool attaches the one or more first wire tools introduced through the first introducer epidural needle within the neuroforaminal space of the spine a selected one level above, one level below and at an adjacent level to the selected right lamina of a targeted vertebra, the one or more first wire tools and the first hook-like grasper tool are pulled through the first exit epidural needle and out of a patient's body, the one or more first wire tools having a curved middle portion, the curved middle portion lying adjacent to the neuroforamen and neuroforaminal canal, the curved middle portion cuts one or more boney structures of the neuroforamen and the neuroforaminal canal 1530 and implementing a plurality of safety mechanisms that include an intraoperative electromyogram, a plurality of nerve conduction studies and one or more nerve sensors to achieve a safe percutaneous environment 1540.

The first hollow internal diameter allows a selected one or more first fluids and first medicines to pass through the first introducer epidural needle. The second hollow internal diameter allows a selected one or more second fluids and second medicines to pass through the second exit epidural needle. The introducer epidural needles are a selected one of a flat tipped introducer epidural needle, a curved introducer epidural needle, a rigid introducer epidural needle, a c-shaped introducer epidural needle, an expandable introducer epidural needle and a flexible introducer epidural needle. The introducer epidural needles have a selected one of a curved penetrating perforating tip and a penetrating perforating straight tip. The introducer epidural needles have a hollow tube that is a protective sheath. The one or more wire tools are a selected one from the group of a guide wire, a thread wire, a bone temperature sensor and a twisted wire. The one or more wire tools are made of a selected one of metal, plastic, nylon and rubber. The one or more wire tools have a selected one of bone cutting and one or more abrasive properties that spare nerves and dura when cutting. The one or more wire tools are utilized to modify tissue, to cut tissue and to cut bone. The one or more wire tools are a selected one of one or more bone-cutting devices, one or more t-saw (Tomita saw) wires, one or more bone cutting wires and a saw device. The one or more wire tools includes an expanding hollow lumen that allows one or more wires, fluids, and medical devices to pass through the expanding hollow lumen. The one or more wire tools includes a plurality of channels and a plurality of apertures to be passed through the expanding hollow lumen to irrigate one or more anatomical areas of the spine. The one or more anatomical areas of the spine are irrigated with cold water. The expanding hollow lumen is made of a selected one of a plastic and a malleable polymer. The one or more wire tools can provide suction. The one or more wire tools are a selected one of left in the epidural space, removed immediately from the epidural space and removed at a later date from the epidural space. The one or more wire tools have a plurality of grooves that pick-up bone debris osteophytes and carry the bone debris osteophytes outside the patient's body by a selected one of pushing and pulling of the one or more wire tools. The one or more wire tools are an expanding balloon. The expanding balloon is a selected one of radio-opaque and radiolucent, the expanding balloon provides a larger target to the exit epidural needle. The one or more wire tools are a selected one of a plurality of pieces and one continuous piece. The one or more wire tools are a selected one of radiolucent and radiopaque. The one or more wire tools are a selected one or more of being magnetic, having one or more electromagnetic capabilities, generating heat, being coupled to a medical device that has a laser eliciting capability, producing a laser, being motorized, vibrating independently and vibrating at one or more calculated rhythms. The epiduroscope has an ultrasound guided capability and a wireless capability to transmit data. The hook-like grasper tools is a pair of grasping forceps. The hook-like grasper tools is a selected one or more of having a fork-shape, having one or more apertures, having a locking device, having a selected one of a closing door and a pinching door, having a sticky substance and having a selected one of magnetic properties and electromagnetic properties. The hook-like grasper tools sutures a selected one of a wire, a lead and a tool at more than one level along the spinal cord, accommodates a pain pump lead and accommodates a spinal cord stimulator lead. The hook-like grasper tools attaches a selected one or more of one or more wires, leads, medical devices and desired target tissue by using a selected one of suture wire, one or more buttons, one or more bolsters, one or more bridges and thread. The method is replicated on one or more spinal cord levels that include cervical, thoracic, lumbar and sacral regions on the patient body. The method is performed under a selected one of X-Ray, fluoroscopy, ultrasound, CT, MRI, and 3D-MRI.

The present invention is a method for performing a percutaneous laminoplasty and a method for performing a percutaneous foraminoplasty. The one or more components and one or more tools utilized for these methods include an introducer needle tool, an exit needle tool, a guide wire tool and a grasper tool. In regards to the term needle, it is defined as any tool or tools that are used to puncture or enter an epidural space or a neuroforaminal space through a percutaneous technique in contrast to open technique and as described for purposes and intentions herein as the T-Technique. The introducer needle tool has an internal diameter that is capable of introducing a guide wire or a thread wire into an epidural space. The introducer needle tool can be rigid, flat tipped, curved, c-shaped, expandable or flexible. The introducer needle has the ability to be inserted, left in during procedure, removed and reinserted into a desired epidural space as a practitioner deems necessary when performing T-Technique. The exit needle can be rigid, flat tipped, curved, c-shaped, expandable or flexible. The terms exit needle or introducer needle can be used interchangeably as it pertains to T-technique described herein. The exit needle tool has an internal diameter that is capable of introducing a grasper catcher tool or other suitable medical tools that may be used to catch guide wire tools as described herein as the T-technique. The term wire can be known interchangeably as a guide wire, a cutting wire, a t-saw or a thread wire, can be rigid, flexible or fluid that has a plurality of functions including navigating inside the patient's body through the epidural space and can be passed to help navigate further into the desired direction towards a desired epidural space or neuroforaminal space where the exit needle is waiting with a grasper tool. The wire can possess tissue modifying capability as well the capability to transport similar tools by coupling and either pulling or pushing medical tools or medical devices to a desired position as well as navigation capability that allows to connect interlaminar epidural spaces with other interlaminar epidural spaces, to connect interlaminar epidural spaces with intervertebral foramen and intervertebral foramen with other intervertebral foramen as described herein in methods known as the T-technique. Furthermore the term wire can represent a tool that can be a hollow tube with holes with an abrasive exterior that allows for air, gas or fluid to be released or removed by vacuum potential, that can be plastic, rubber, non-metallic or metallic and can vary in size. The wire can be further described and function as a guide wire, thread saw, a connecting device that allows other tools to be pulled into a desired location, cutting wire, or can represent any suitable tissue modifying tool utilized during T-technique process and methods described herein in accordance with one embodiment of the present invention.

The wire has bone and target tissue cutting and molding capabilities or can connect to a bone-cutting device or saw device through its coupling capability. The wire can be hollow to allow the passage of another material or guide wire through it. The distal end or proximal end of the guide wire can have magnetic properties to attract one or more forceps and grasping tools with similar attracting magnetic properties. The wire can made of any number of suitable materials including plastic, metal, minerals, rubber, and allow for the passage of fluids or gases through it. The wire can have apertures that allow leakage of fluid or gas for irrigation. The wire can also have suctioning capability and have grooves that can pick-up bone debris osteophytes and bring the debris osteophytes outside of the patient's body following pulling or pushing of the wire. The wire or guide wire can also be a hollow tube made of a malleable plastic like material that can permit other guide wires or wires or medical tools or devices to pass through it. The cutting wire tool device can have access to heat and can be construed to allow a laser to be attached or be capable of producing a laser. It can be motorized, have the ability to vibrate, and can be encapsulated in order to protect vital structures from damage from sharp edges because of poor placement, unforeseen movements or malfunction of the device. The thread wire can have a protective covering that can be used to preserve tissue where cutting is not desired during sawing action. The protective covering can be a plastic covering that allows for guide wires to move freely within it. The protective covering can be absorbed into the patient's body or be manually removed, and can be rubbed off with friction. The protective covering can be disposed on the entire thread wire or in a plurality of desired locations along the thread wire such as over the cutting portion of the wire. The encapsulation on the wire saw can be rubbed off with friction as the wire comes in contact with bone or target tissue during cutting. Furthermore, the encapsulation can manually be removed at an optimal position and time during the procedure, can expand manually and independently, can be removed independently and manually, can shrink or decrease in size manually, independently or with applied force, or absorb into a body system without damage or disintegrate with time. The encapsulation can be made to have one or more hooks or magnets attached to a pulley device to be removed.

The guide wires include a plurality of cutting and abrasive components and can be made of an expanding lumen, can be radiolucent or radiopaque, can be magnetic or have electromagnetic capabilities and can have a tip at a proximal end or a distal end that can have multiple purposes including a balloon that can expand once placed in a desired location. The balloon can be radiopaque or radiolucent, and can be expanded in a desired location to create a larger target for an exit epidural needle catcher grasper tool to be located while under fluoroscopy or other imaging study that can assist a practitioner in locating and performing a task. The balloon can be retracted, expanded, have several lumens for utility, can have a plurality of different levels of opacity or lucency to help identify the depth of a balloon when inside the body, epidural space or neuroforaminal space. The balloon can have different radiolucent or opaque shapes and designs engraved on its exterior and can absorb a grasper tool such as a hook and bring an attached absorbed thread wire exteriorly out of the patient's body. The tip of the guide wire can be a balloon or another similarly expanding tool that can conjoin to a catcher tool or can be caught by a grasper tool that has been passed through an exit needle. After the wire has been caught by a grasper tool, the grasper tool is now in control of the wire and can reverse in direction and exit the exit needle tool which it came into the patient's body from and pull the wire that it has secured out of the patient's body through the exit needle. The exit needle or capturing needle has an internal diameter capable to allow epiduroscopes, catchers, grasper tools, forceps, flexible graspers and/or one or more hook like devices or a bone temperature sensor to pass within and through into epidural space or neuroforaminal space where described medical tools and devices can catch the wire, guide wire or cutting wire or tissue modifying wire and pull it outside the body. Optionally grasping forceps, a holder tool or a hook can be passed through an epiduroscope that can be passed through the exit needle. The terms and functionality of the exit needle or the introducer needle can be used interchangeably and can possesses a US (ultrasound) guided tip that can define structures while in the epidural space and the transforaminal space. Furthermore image enhancing tools such as x-ray imaging, fluoroscopy, CT, MRI, and US technology can assist a practitioner to perform such tasks as required by one or more epidural introducer tools and exit needle tools for methods described herein as the T-technique.

A hollow tube known as a vessel tool can be passed between the introducer and the exit epidural needles with the T-Technique. The hollow tube can be made of rubber or plastic, can be flexible or rigid, contouring, absorbable, penetrable, have a plurality of apertures, can be a plurality of pieces or one continuous piece, can allow for passage and placement of one or more guide wires, can act as a protective sheath for a guide wire, can allow fluid to pass though, can have suctioning capability, can allow one or more gases to pass through and can be used as a medium for transfer of medical tools and devices. The hollow tube can allow fluid to pass through in an effort to cool the thread wire while cutting. The hollow tube can have suction applied to either end to remove fluid from a field environment during the procedure. An epidural drain catheter can be passed in one space above or below the procedure site through an epidural needle tool and the catheter can be attached to negative pressure suction located outside of the body so as to drain any possible blood or fluid collected in the epidural space. The drain catheter can be left in the space after the procedure, removed immediately or removed at a later date.

The methods also utilize a grasping forceps tool that can be in any suitable form and can be flexible or non-flexible. The grasping forceps tool is used to interlock or connect while positioned in an epidural space or neuroforaminal space to a related wire that is passed from an introducer needle by the T-technique. Once the grasper tool has made the catch or connection with the guide wire it can now be pulled through the exit needle outside the patient's body. The grasping forceps can be a hook mechanism, with a fork-shape, have an aperture, a locking device, a closing or pinching door, can be a sticky substance, can have magnetic or electromagnetic properties and/or have an attractive force that can attract the distal end of the guide wire to the grasping forceps. The grasping forceps can have a coating where an US (ultrasound machine outside the body) could be used to determine the distance between the grasping forceps and the guide wire. Locking or catching the guide wire can also be done under Fluoroscopy, with an US, a CT, an MRI, a 3-Dimensional MRI or other suitable imaging studies that can assist the practitioner in completing such a task.

Alternatively, the grasper tool can also possess the ability to suture a wire, a lead or a tool at more than one level along the spinal cord such as leads for a pain pump or leads for a spinal cord stimulator and tie them to other wires, leads, medical devices or desired target tissue by using suture wire, buttons, bolsters, bridges, thread or similar surgical tools and devices. This is one of the most common causes of failure of spinal cord stimulators that include lead breakage and lead migration. In application of the T-technique, the grasper tool can be used for lead placement and fastening of both the distal and proximal ends of the leads. This process will allow a practitioner to access both the distal and proximal ends of the leads or wires as well as at any point along the spine where there is access to wires, leads, devices and target tissue through the described T-technique where the grasper tool enters the exit needle or the introducer needle to access the neuroforaminal space and/or epidural space at any target level of the spine.

An epiduroscope or a fiberscope with fiber optic capability, can be passed through epidural needles and placed in the epidural space, the extra epidural space or the neuroforaminal space and can be left in place for direct vision while utilizing the T-Technique. The epiduroscope or fiberscope can be one continuous piece or a plurality of pieces working together from an introducer needle to an exit needle with one continuous point of visualization, a single point of visualization or a plurality of points of visualization. The epiduroscope or fiberscope can also have one or more ultrasound guided capabilities and one or more wireless capabilities for data transmission. The scope can have an option to allow a cutting instrument to pass through to perform cutting or the scope can itself be used as a cutting device by using a saw, a blade, a laser, heat energy or other suitable cutting device. The scope can have the ability to pass fluids, medical tools or materials, medically useful gases or substances with medicinal benefit in desired target areas. The scope can have a light source in many locations, a single location or a continuous location. The scope can have a lumen or a plurality of lumens to allow materials such as gas, fluids, or medical tools such as guide wires, grasper tools or probes to pass through and position them in the desired target areas.

Additionally a catheter with an inflatable tip balloon like structure can be passed through an epiduroscope or fiberscope through its working channel or lumen or through one or more introducer or exit epidural needles. The balloon structure can expand from addition of gas or liquids. Furthermore the inflatable balloon can be placed in such a position that it remains as a shield between the cutting wire and vital anterior structures like exiting nerves and dura. The inflatable balloon can be designed to expand first laterally and then posteriorly so that it does not exert more pressure on dura and may help to push cut lamina posteriorly (outwards) following cuts from the T-Technique. The inflated balloon can be deflated and taken out after the procedure or left in the epidural space as a support structure or other suitable utility or be absorbed by the patient's body. The inflated balloon can have a plurality of grooves on its posterior surface to accommodate a cutting wire to have better control during cutting. The inflated balloon can have radiopaque properties or can be injected with contrast material so that its placement is well visualized under fluoroscopy. Additionally the patient will be awake during T-Technique percutaneous procedures giving a practitioner immediate awareness if neural structures are being encroached upon by immediate paresthesia felt and reported by a patient, which would prompt immediate cessation and an alternative approach which is a common practice in the field of pain management. The application of current safety mechanisms such as intraoperative EMG (Electromyography), NCS (Nerve conduction studies) and nerve sensors can be used to achieve a desired safe procedural environment. Ultrasound technology, radiofrequency, CT, MRI, 3-dimensional MRI, C-Arm or other suitable instruments can be used in assistance to complete the task to identify surface anatomy and distance between neural structures, thread wire and other medical tools.

The present invention also includes a method for fixing, fusing and lifting loose bone following an applied T-Technique. The method includes a technique to secure the spinous process of a target vertebra with a modified spinous process screw tool. The spinous process is a relatively superficial bony structure in the spine and can be easily felt under the skin. The spinous process can easily be approached percutaneously with a modified percutaneous spinous process screw tool, an epiduroscope or other similar percutaneous drilling devices. The modified spinous process screw tool that is percutaneously inserted into a spinous process and then fixated with a locking, rotating screwing motion, where a plurality of teeth like protrusions, insertions or hooks attach the screw tool to the spinous process. The spinous process modified screw and a plurality of other suitable types of screw tools regarding the T-Technique can also be made of implantable material such as stainless steel, titanium and other suitable biocompatible materials. The spinous process screw tool is attached to a gauge tool outside of the patient's body that can adjust the desired outward (posterior) pressure on loose bone manually or automatically and can adjust and assist in maneuvering a cut portion of the bone into a desired position. The screw tool can have one or multiple apertures, one or multiple lumens, hooks or ports that can attach to one or more wires, bars, needles, other screws or tools for anchoring or other utility. The modified spinous process screw tool allows a practitioner to maneuver, move and adjust loose bone that has been cut by the T-Technique. The modified spinous process method for modeling and maneuvering loose bone can be equally applied by both percutaneous T-technique laminoplasty and foraminoplasty. An example of loose bone in a case of percutaneous laminoplasty by T-Technique would be defined as target vertebral bone medial to the cuts of its right lamina and its left lamina. In this example the loose bone would include the right lamina, spinous process and left lamina of the target vertebral bone. Following cuts to the target lamina, the loose bone is no longer attached continuously with the original anatomy of the target vertebra and is now fully free to be mobilized by application of posterior (outward) force and pressure by a modified spinous process screw tool attached to a gauge tool outside of the patient's body. Following fixation of a spinous process screw tool into spinous process by methods described herein, posterior (outwards) pressure is applied that can allow loose bone to be placed in a desired position that will allow for expansion of the spinal canal and neuroforamen by the T-Techniques. The maneuvering will achieve decompression by creating space for the neural elements. The loose bone now in place will be secured using the subsequent tools, percutaneous fusion and methods that will lead to osteogenesis between the cut ends of lamina where healing and fusion will take place.

There is also an optional percutaneous method for loose bone lifting and fixation that utilizes a plurality of M Technique steps. The M Technique requires the use of a plurality of modified pedicle screws and a plurality of modified fixing screws. Following T-Technique laminoplasty or foraminoplasty, a percutaneous modified spinous process screw will be placed into target tissue where the distal end of the screw will be inserted into spinous process and the proximal end will protrude and have an exit from the skin of the patient. Pressure will be applied in a posterior direction with the use of a pressure gauge tool that is positioned outside the body that is attached to the spinous process screw. The posterior pressure placed on the modified spinous process screw though utility of the gauge tool will be sufficient to protect the canal from anterior drift as well as properly place the cut lamina in a desired position to alleviate foraminal and/or canal stenosis. Subsequently the M technique follows by percutaneously inserting one modified pedicle screw through each pedicle of a chosen target vertebra in the AP position, (for example: vertebral level 5 has one modified pedicle screw in a right pedicle and one modified pedicle screw in a left pedicle). The modified pedicle screw can have the possibility of angulation or curvature where the distal end of the screw will be inserted into target tissue and fastened into the pedicle by percutaneous methods and the proximal end can have the capability to interlock into one or more other screws or tools. The length of the modified pedicle screw can be variable and can be increased through an interlocking feature that will extend to a desired needed length. The proximal end of the modified pedicle screw will have one or more openings through which a fusing screw tool can be passed through and interlock with it. The fusing screw can be expandable by both automatic, or manual technique, can decrease in size, can vibrate, can contain fluid, can absorb fluid, can have drilling or puncturing capability independently or with a practitioner's assistance such as a screwing rotation that can elicit a drilling or a puncturing capability or a plurality of teeth-like, nail-like projections to enter the touching structures and attach to them, can have one or more rotational capabilities and will not only separate target tissue but likewise keep it in a secured position. The fusing screw tool can use the modified pedicle screw for support as it interlocks with the proximal end of the modified pedicle screw percutaneously. The fusing screw can interlock with the modified pedicle screw at any point along the fusing screw. The distal end of the fusing screw will target the loose bone seen following cutting as described in T-technique foraminoplasty and/or laminoplasty. The fusing screws can be angled towards the loose bone and subsequently fastened into target tissue to secure the lamina and loose bone into its new position. After several weeks following fusion and healing, the screws can be removed as needed.

What is claimed is:

1. A method for performing a percutaneous laminoplasty, the method comprising the steps of:
    entering a first needle percutaneously from outside a patient into an epidural space superior to a selected lamina, wherein the first needle includes a first lumen extending therethrough between a proximal end and a distal end, and wherein the distal end of the first needle comprises a perforating tip;
    entering a second needle percutaneously from outside the patient into the epidural space inferior to the selected lamina, wherein the second needle includes a second lumen extending therethrough between a proximal end and a distal end, and wherein the distal end of the second needle comprises a perforating tip;
    introducing a wire cutting tool into the proximal end of the first lumen of the first needle at the epidural space superior to the selected lamina and advancing the wire cutting tool through the first needle and out of the distal end of the first needle into the epidural space superior to the selected lamina;
    introducing a grasper tool into the proximal end of the second lumen of the second needle at the epidural space inferior to the selected lamina and advancing the grasper tool through the second needle and out of the distal end of the second needle into the epidural space inferior to the selected lamina;
    actuating the grasper tool to temporarily couple a distal end of the wire cutting tool in the epidural space after the wire cutting tool and the grasper tool have been introduced into the epidural space;
    proximally retracting the grasper tool from the epidural space and out from the proximal end of the second needle to proximally retract the wire cutting tool through the second needle and out from the proximal end of the second needle; and
    manipulating the wire cutting tool, by moving the wire cutting tool around the selected lamina, to modify the selected lamina.

2. The method of claim 1, further comprising: implementing a safety mechanism selected from the group consisting of an intraoperative electromyogram, a nerve conduction study, and a nerve sensor.

3. The method of claim 2, further comprising: passing fluids or medicines through the first or second lumens for delivery to the epidural space of the selected lamina.

4. The method of claim 3, wherein the step of manipulating the wire cutting tool further comprises cutting at least a portion of the selected lamina.

5. The method of claim 4, wherein the wire cutting tool is selected from the group consisting of a guide wire, a thread wire, a bone temperature sensor, a twisted wire, a suction-providing wire, and an expanding balloon.

6. The method of claim 5, wherein the wire cutting tool is made from metal, plastic, nylon, or rubber.

7. The method of claim 6, wherein the distal end of the grasper tool temporarily couples the wire tool with a hook-like grasper.

8. The method of claim 6, further comprising: removing bone debris osteophytes by manipulating the wire cutting tool.

9. The method of claim 6, wherein one of the first or second needles is configured to accommodate inserting a pain pump catheter or spinal cord stimulator lead into the needle.

10. A method for performing a percutaneous laminoplasty, the method comprising the steps of:
    entering a first needle percutaneously from outside a patient into an epidural space inferior to a selected lamina, wherein the first needle includes a first lumen extending therethrough between a proximal end and a distal end, and wherein the distal end of the first needle comprises a perforating tip;
    entering a second needle percutaneously from outside the patient into the epidural space superior to the selected lamina, wherein the second needle includes a second lumen extending therethrough between a proximal end and a distal end, and wherein the distal end of the second needle comprises a perforating tip;
    introducing a wire cutting tool into the proximal end of the first lumen of the first needle at the epidural space inferior to the selected lamina and advancing the wire cutting tool through the first needle and out of the distal end of the first needle into the epidural space inferior to the selected lamina;
    introducing a grasper tool into the proximal end of the second lumen of the second needle at the epidural space superior to the selected lamina and advancing the grasper tool through the second needle and out of the distal end of the second needle into the epidural space superior to the selected lamina;
    temporarily coupling a distal end of wire cutting tool with the grasper tool in the epidural space after the wire cutting tool and the grasper tool have been introduced into the epidural space;
    proximally retracting the grasper tool from the epidural space and out from the proximal end of the second needle to proximally retract the wire cutting tool through the second needle and out from the proximal end of the second needle; and
    manipulating the wire cutting tool, by moving the wire cutting tool around the selected lamina, to modify the selected lamina.

11. The method of claim 10, further comprising: implementing a safety mechanism selected from the group consisting of an intraoperative electromyogram, a nerve conduction study, and a nerve sensor.

12. The method of claim 11, further comprising: passing fluids or medicines through the first or second lumens for delivery to the epidural space of the selected lamina.

13. The method of claim 12, wherein the step of manipulating the wire cutting tool further comprises cutting at least a portion of the selected lamina.

14. The method of claim 13, wherein the wire cutting tool is selected from the group consisting of a guide wire, a thread wire, a bone temperature sensor, a twisted wire, a suction-providing wire, and an expanding balloon.

15. The method of claim 14, wherein the wire cutting tool is made from metal, plastic, nylon, or rubber.

16. The method of claim 15, wherein the distal end of the grasper tool temporarily couples the wire cutting tool with a hook-like grasper.

17. The method of claim 15, further comprising: removing bone debris osteophytes by manipulating the wire cutting tool.

18. The method of claim 15, wherein one of the first or second needles is configured to accommodate inserting a pain pump catheter or spinal cord stimulator lead into the needle.

* * * * *